(12) United States Patent
Panunzio et al.

(10) Patent No.: US 7,858,780 B2
(45) Date of Patent: *Dec. 28, 2010

(54) PROCESS FOR THE PREPARATION OF (S)-(+)-10,11-DIHYDRO-10-HYDROXY-5H-DIBENZ (B,F)AZEPINE-5-CARBOXAMIDE

(75) Inventors: Mauro Panunzio, Treviglio (IT); Eileen Campana, Treviglio (IT); Sabatino Pulcini, Treviglio (IT); Gabriele Breviglieri, Treviglio (IT)

(73) Assignee: Farchemia S.R.L., Treviglio (IT)

( * ) Notice: Subject to any disclaimer, the term of this patent is extended or adjusted under 35 U.S.C. 154(b) by 385 days.

This patent is subject to a terminal disclaimer.

(21) Appl. No.: 11/791,582

(22) PCT Filed: Nov. 15, 2005

(86) PCT No.: PCT/EP2005/012205

§ 371 (c)(1),
(2), (4) Date: Sep. 24, 2008

(87) PCT Pub. No.: WO2006/056339

PCT Pub. Date: Jun. 1, 2006

(65) Prior Publication Data

US 2009/0105472 A1    Apr. 23, 2009

(30) Foreign Application Priority Data

Nov. 26, 2004 (IT) ............................ MI2004A2291

(51) Int. Cl.
*C07D 223/28* (2006.01)

(52) U.S. Cl. ..................................... 540/589; 540/591
(58) Field of Classification Search ................. 540/589, 540/591
See application file for complete search history.

(56) References Cited

U.S. PATENT DOCUMENTS 6,384,217 B1    5/2002    Atilio et al.

FOREIGN PATENT DOCUMENTS

| EP | 1 127 877 A2 | 8/2001 |
| IT | 2004002230 A | 11/2004 |
| WO | WO 02/096881 A1 | 12/2002 |

OTHER PUBLICATIONS

Database Beilstein [Online] Beilstein Institut zur Forderung der Chemischen Wissenschaften; XP002374960; Database accession No. 3620473, 3620675, Abstract & D. Kikelj et al.: Synth Commun. vol. 14, No. 6, 1984, pp. 547-556.

Benes et al., "Anticonvulsant and Sodium Channel-Blocking Properties of Novel 10,11-Dihydro-5H-dibenz[b,f]azepine-5-carboxamide Derivatives", J Med Chem 42:2582-2587 (1999).

*Primary Examiner*—Brenda L Coleman
(74) *Attorney, Agent, or Firm*—Porzio, Bromberg & Newman, P.C.

(57) ABSTRACT

(S)-(+)-10,11-Dihydro-10-hydroxy-5H-dibenz[b,f]azepine-5-carboxyamide is prepared starting from racemic 5-cyano-10,11-dihydro-10-hydroxy-5H-dibenz[b,f]azepine by phtaloylation, separation of the diastereomeric salts of the phthaloyl derivative with (S)-phenylethylamine, hydrolysis of the (S, S) salt to (S)-(+)-5-cyano-10,11-dihydro-10-hydroxy-5H-dibenz[b,f]azepine and hydrolysis of the nitrile group of the latter to amido group, by treatment with peroxy compounds in alkali medium.

4 Claims, No Drawings

PROCESS FOR THE PREPARATION OF (S)-(+)-10,11-DIHYDRO-10-HYDROXY-5H-DIBENZ (B,F)AZEPINE-5-CARBOXAMIDE

CROSS REFERENCE TO RELATED APPLICATION

This is a National Stage of International Application No. PCT/EP2005/012205, filed Nov. 15, 2005, which claims the benefit of Application No. MI2004A002291, filed in Italy on Nov. 26, 2004, the disclosures of which Applications are incorporated by reference herein.

The present invention relates to a novel process for the preparation of (S)-(+)-10,11-dihydro-10-hydroxy-5H-dibenz[b,f]azepine-5-carboxamide, of formula 2,

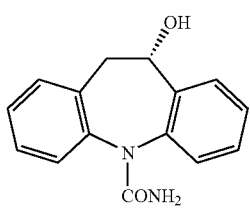

(2)

starting from racemic 5-cyano-10,11-dihydro-10-hydroxy-5H-dibenz[b,f]azepine, of formula 1

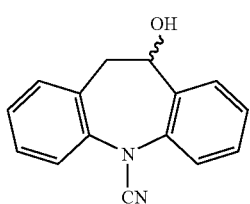

(1)

(S)-(+)-10,11-Dihydro-10-hydroxy-5H-dibenz[b,f]azepine-5-carboxamide 2 is an intermediate for the synthesis of antiepilectic drugs: see the paper of J. Benès et al. in *J. Med. Chem.* 1999, 42, 2582-2587 (see also WO 02/096881) which discloses the preparation of said compound 2 by esterification of racemic 10,11-dihydro-10-hydroxy-5H-dibenz[b,f]azepine-5-carboxamide with mentyloxyacetic acid, separation of the resulting diastereomers and hydrolysis of the respective mentyloxyacetate.

It has now been found that (S)-(+)-10,11-dihydro-10-hydroxy-5H-dibenz[b,f]azepine-5-carboxamide 2 can advantageously be prepared starting from racemic 5-cyano-10,11-dihydro-10-hydroxy-5H-dibenz[b,f]azepine 1 (disclosed and claimed in EP 1,127,877 and U.S. Pat. No. 6,384,217, both in the Applicant's name), by esterification of compound 1 with phthalic anhydride and transformation of the resulting phthaloyl derivative 3, by salification with (S)-1-phenylethylamine, into diastereomers 4 and 5 which by crystallization afford diastereomer 4 (in marked excess—10:1—compared with 5). From compound 4, by liberation of the phthaloyl derivative 6, (S)-(+)-5-cyano-10,11-dihydro-10-hydroxy-5H-dibenz[b,f]azepine 7 is obtained, which can easily be hydrolysed to (S)-(+)-10,11-dihydro-10-hydroxy-5H-dibenz[b,f]azepine-5-carboxamide 2 by treatment with peroxides in alkali medium, according to Italian Patent application N. MI2004A002230 in the Applicant's name. The process of the present invention affords, inter alia, the important advantage of making use of the intermediate (S)-1-phenylethylamine which is of common use and at least ten times less expensive than mentyloxyacetic acid used in the known technique. This process is summarized in the following scheme:

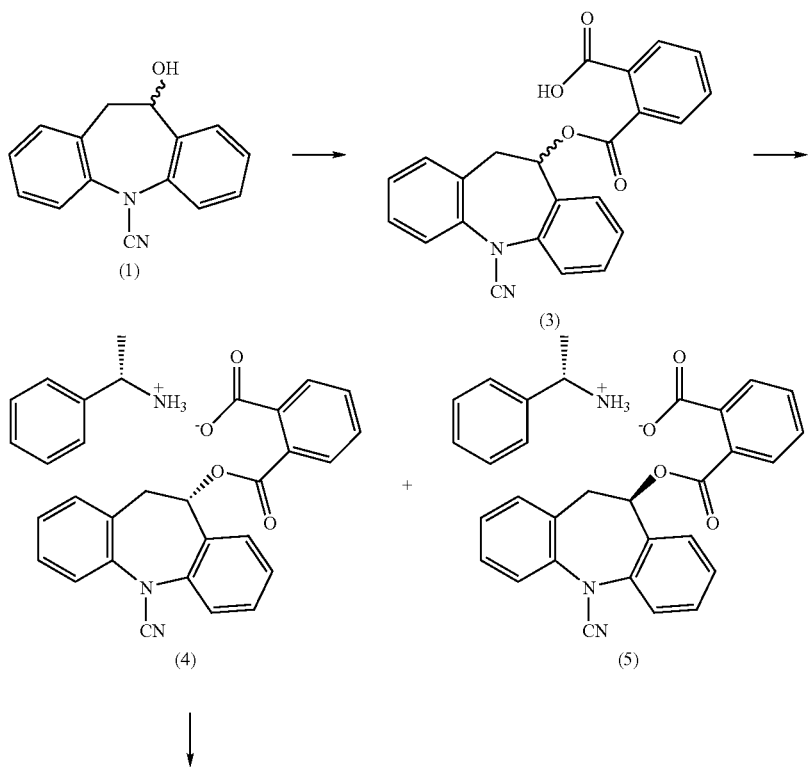

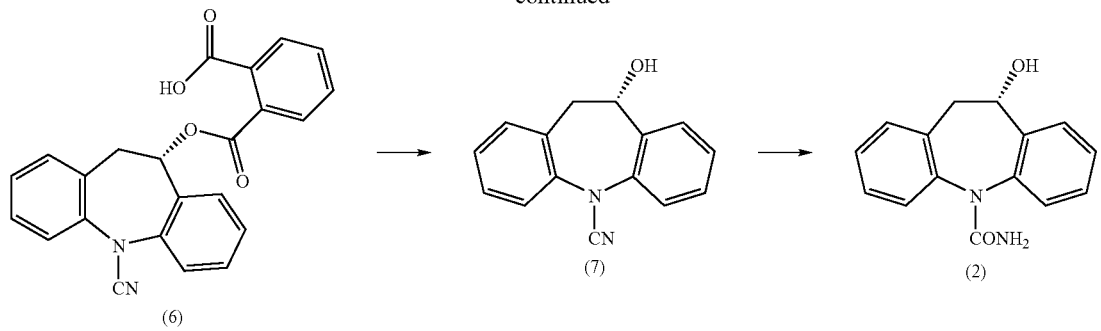

Phthaloylation of nitrile 1 is suitably carried out in inert solvents, e.g. chlorinated solvents such as dichloromethane, chloroform and the like, with an amount of phthalic anhydride ranging from 1 to 1.5 (preferably approx. 1.2) mols compared with nitrile 1, in the presence of a slight molar excess of pyridine (to phthalic anhydride) and of 4-dimethylaminopyridine in catalytic amounts. After completion of the reaction, the mixture is acidified at a temperature of 10-25° C., the organic phase is evaporated off and the phthaloyl derivative 3 is recovered, suspended in a lower alcohol and treated with a substantially equimolar amount of (S)-1-phenylethylamine. The solvent is evaporated off and the residue is recrystallized from mixtures of lower chloroalkanes and alicyclic hydrocarbons, e.g. dichloromethane/cyclohexane, to obtain a product consisting of diastereomers 4 and 5 in a 91/9 ratio, which is treated with aqueous alkali. (S)-1-Phenylethylamine can be recovered by extraction with a water-immiscible or sparingly water-miscible solvent (e.g. diethyl ether or diisopropyl ether), whereas acidification of the aqueous phase and extraction with a water-immiscible or sparingly water-miscible solvent affords (without isolating intermediate 6) (S)-(+)-5-cyano-10,11-dihydro-10-hydroxy-5H-dibenz[b,f]azepine 7 of optical purity higher than 90%. The latter, according to the process of Italian Patent application N. MI2004A002230, yields the final carboxyamide 2 with optical purity higher than 95%.

The novel compounds of formulae 3 (and related enantiomers), 4, 5 and 7, are also an object of the present invention.

The following examples illustrate the process according to the invention.

EXAMPLE 1

Preparation of 5-cyano-10,11-dihydro-10-hydroxy-5H-dibenz[b,f]azepine phthalic ester 33.5 g of phthalic anhydride in 500 ml of methylene chloride are added with 47 g of 5-cyano-10,11-dihydro-10-hydroxy-5H-dibenz[b,f]azepine 1,1 g 4-dimethylaminopyridine and 17.5 g of pyridine. The reaction is slightly exothermic (temperature raises from 15° C. to 19° C.). The mixture is kept at 30-35° C. for one hour, cooled to 15° C. and added with 100 ml of 2.5M hydrochloric acid. The organic phase is washed with 50 ml of water and then evaporated under vacuum to obtain 75 g of 5-cyano-10-hydroxy-10,11-dihydro-5H-dibenz[b,f]azepine phthalic ester 3, m.p. 169-171° C.

EXAMPLE 2

Preparation of (S)-1-phenylethylamine diastereomeric salts

A suspension of 5 g of 5-cyano-10,11-dihydro-10-hydroxy-5H-dibenz-[b,f]azepine phthalic ester 3 in 55 ml of MeOH is very slowly added drop by drop with a solution of 1.58 g of (S)-1-phenylethylamine in 5 ml of MeOH. The solution remains homogeneous during the addition. After keeping at room temperature for 30 min., the solvent is evaporated off under reduced pressure thereby obtaining 7.0 g of a white solid, which is dissolved in 40 ml of $CH_2Cl_2$, then added with 50 ml of cyclohexane. After standing overnight, the resulting crystal is filtered and washed with cyclohexane to afford 2.4 g of a white crystalline product, consisting of a mixture of the two diastereomers 4 and 5 in a 91/9 (S,S)/(S,R) ratio (HPLC analysis).

EXAMPLE 3

(S)-(+)-5-Cyano-10,11-dihydro-10-hydroxy-5H-dibenz[b,f]azepine (7)

2.4 g of the salt of Example 2, dissolved in water (20 ml), are added at room temperature with 0.19 g of NaOH dissolved in 5 ml of $H_2O$. The mixture is left under stirring for 30-45 min. The resulting solution is extracted with ethyl ether (3×10 ml) to remove phenylethylamine (72% recovery). The aqueous basic phase is acidified with dil. HCl to acid pH of approx. 3-4 (turns cloudy) then extracted with $CHCl_3$ for 3 times, dried and concentrated, to obtain 1.8 g of product (100% yield) free from amine, consisting of (S)-(+)-5-cyano-10,11-dihydro-10-hydroxy-5H-dibenz[b,f]azepine 7, with 91% optical purity, by HPLC analysis.

EXAMPLE 4

(S)-(+)-10,11-Dihydro-10-hydroxy-5h-dibenz[b,f,]-azepine-5-carboxyamide (2)

A mixture of the product of Example 3 (267 mg, 0.69 mmol) dissolved in EtOH (10 ml) and $H_2O$ (5 ml) is added with sodium perborate (427 mg, 2.78 mmol), left at room temperature for 12 h, then added with a further 215 mg of perborate and refluxed for 15 h. pH is adjusted to 14 with a few drops of 0.1N NaOH and the mixture is left to stand in the warmth for 30 min. Part of the ethanol is removed under reduced pressure and the aqueous residue is extracted with ethyl acetate, dried and concentrated. The resulting white solid is dissolved in methanol, treated with a few ml of hexane, then concentrated to afford 129 mg (72%) of (S)(+)-10,11-dihydro-10-hydroxy-5H-dibenz[b,f,]azepine-5-carboxyamide 2, with 95% optical purity.

EXAMPLE 5

(S)-(+)-10,11-dihydro-10-hydroxy-5H-dibenz[b,f,]-azepine-5-carboxamide (2)

The product of Example 3 (500 mg, 1.3 mmol), dissolved in EtOH (5 mL), is dropwise added with a 3M $K_2CO_3$ solution (5 mL), then with 35% hydrogen peroxide (1.5 ml), at 0° C. After 30 min. at room temperature, the transformation of nitrile group to amide is completed by heating under reflux, adjusting pH to 14 with few drops of 0.1N NaOH. The reaction mixture is cooled at room temperature for two hours, then concentrated under reduced pressure. The residue is extracted with chloroform (3×50 mL) and dried over potassium carbonate. The solvent is evaporated off to afford compound 2 (320 mg, 96% yield), with 95% optical purity (HPLC analysis).

The invention claimed is:

1. A process for the preparation of (S)-(+)-10,11-dihydro-10-hydroxy-5H-dibenz[b,f]azepine-5-carboxamide of formula 2

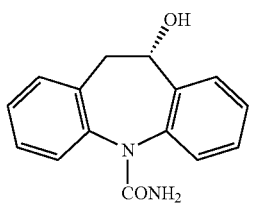
(2)

characterized in that the nitrile group of (S)-(+)-5-cyano-10,11-dihydro-10-hydroxy-5H-dibenz[b,f]azepine of formula 7

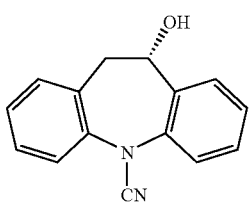
(7)

is hydrolyzed with peroxy compounds in alkali medium.

2. The process as claimed in claim 1, characterized in that (S)-(+)-5-cyano-10,11-dihydro-10-hydroxy-5H-dibenz[b,f] azepine of formula 7 is in turn prepared starting from racemic 5-cyano-10,11-dihydro-10-hydroxy-5H-dibenz[b,f]azepine of formula 1 by phthaloylation, salification of the phthaloyl derivative of formula 3 with (S)-1-phenylethylamine, separation of the resulting diastereomeric salts 4 and 5 and hydrolysis of the salt 4, according to the following scheme:

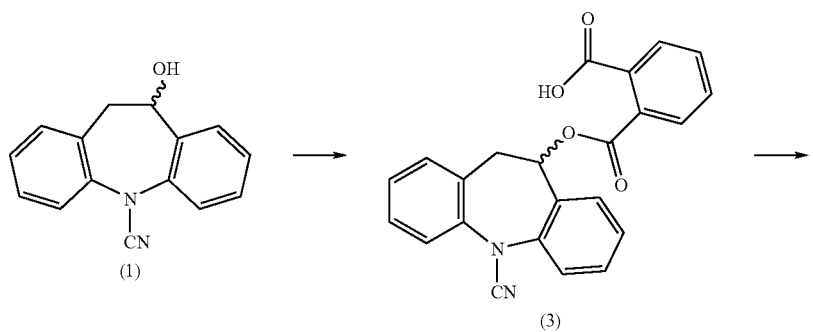

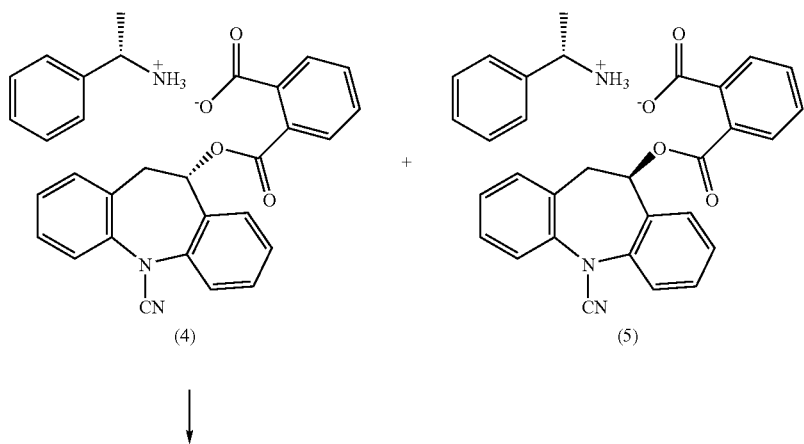

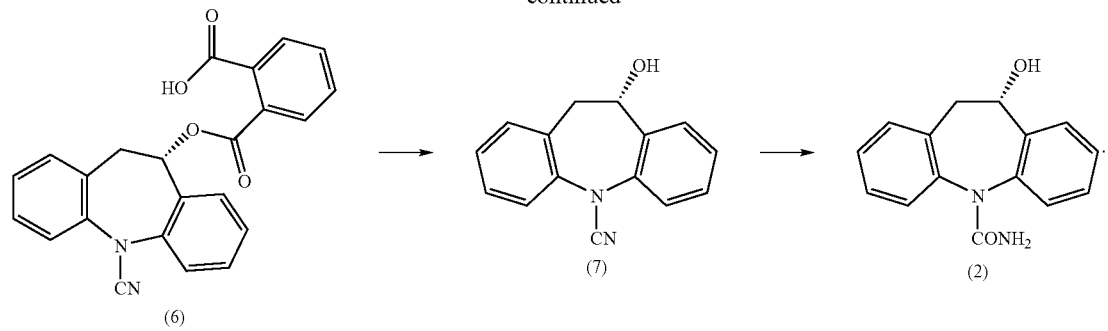
3. The process as claimed in claim 2, characterized in that the diastereomeric salts 4 and 5 are separated by crystallization from mixtures of lower chloroalkanes and alicyclic hydrocarbons.
4. The process as claimed in claim 2, characterized in that the diastereomeric salts 4 and 5 are separated by crystallization from mixtures of dicholoromethane and cyclohexane.
* * * * *